United States Patent
Gent

[19]

[11] Patent Number: 5,988,851
[45] Date of Patent: Nov. 23, 1999

[54] MEDICAL TREATMENT AND OR DIAGNOSTIC SYSTEM

[75] Inventor: Hartmut Gent, Erlangen, Germany

[73] Assignee: Siemens Aktiengesellschaft, Munich, Germany

[21] Appl. No.: 08/897,117

[22] Filed: Jul. 18, 1997

[30] Foreign Application Priority Data

Jul. 18, 1996 [DE] Germany .......................... 196 29 093

[51] Int. Cl.⁶ .................................................. G06F 19/00
[52] U.S. Cl. .......................... 364/188; 364/192; 364/146
[58] Field of Search .................................. 364/188, 189, 364/190, 191, 192, 413.13

[56] References Cited

U.S. PATENT DOCUMENTS

| | | | |
|---|---|---|---|
| 4,731,725 | 3/1988 | Suto et al. | 364/413 |
| 4,922,909 | 5/1990 | Little et al. | 128/630 |
| 5,287,514 | 2/1994 | Gram | 345/333 |
| 5,627,747 | 5/1997 | Melton et al. | 364/188 |

FOREIGN PATENT DOCUMENTS 19520170 5/1996 Germany .

*Primary Examiner*—Albert De Cady
*Assistant Examiner*—Esaw Abraham
*Attorney, Agent, or Firm*—Sughrue, Mion, Zinn, Macpeak & Seas, PLLC

[57] ABSTRACT

A medical system e.g. for diagnosing and/or treating a patient has a system controller for controlling the system-specific components. The controller works together with an input device and is additionally assigned a data storage unit in which it is possible to store at least one operating menu. The operating menu can be called up by means of the input device and can be displayed on an indicating or display device. The operating menu includes a plurality of operating functions which can be selected, e.g., by means of a movable marker. When an operating function is selected its associated executable function is executed under control of the system controller. The system is further provided with the functionality of allowing a user to freely select specific operating functions from among the totality of operating functions assigned to the one or more operating menus and store the selected functions in the data storage device grouped as a separate, independent operating menu. This independent operating menu can thereafter be displayed as a separate menu on the indicating or display device and utilized as a more direct means for executing those functions grouped with the independent operating menu.

16 Claims, 6 Drawing Sheets

FIG. 4
CONVENTIONAL
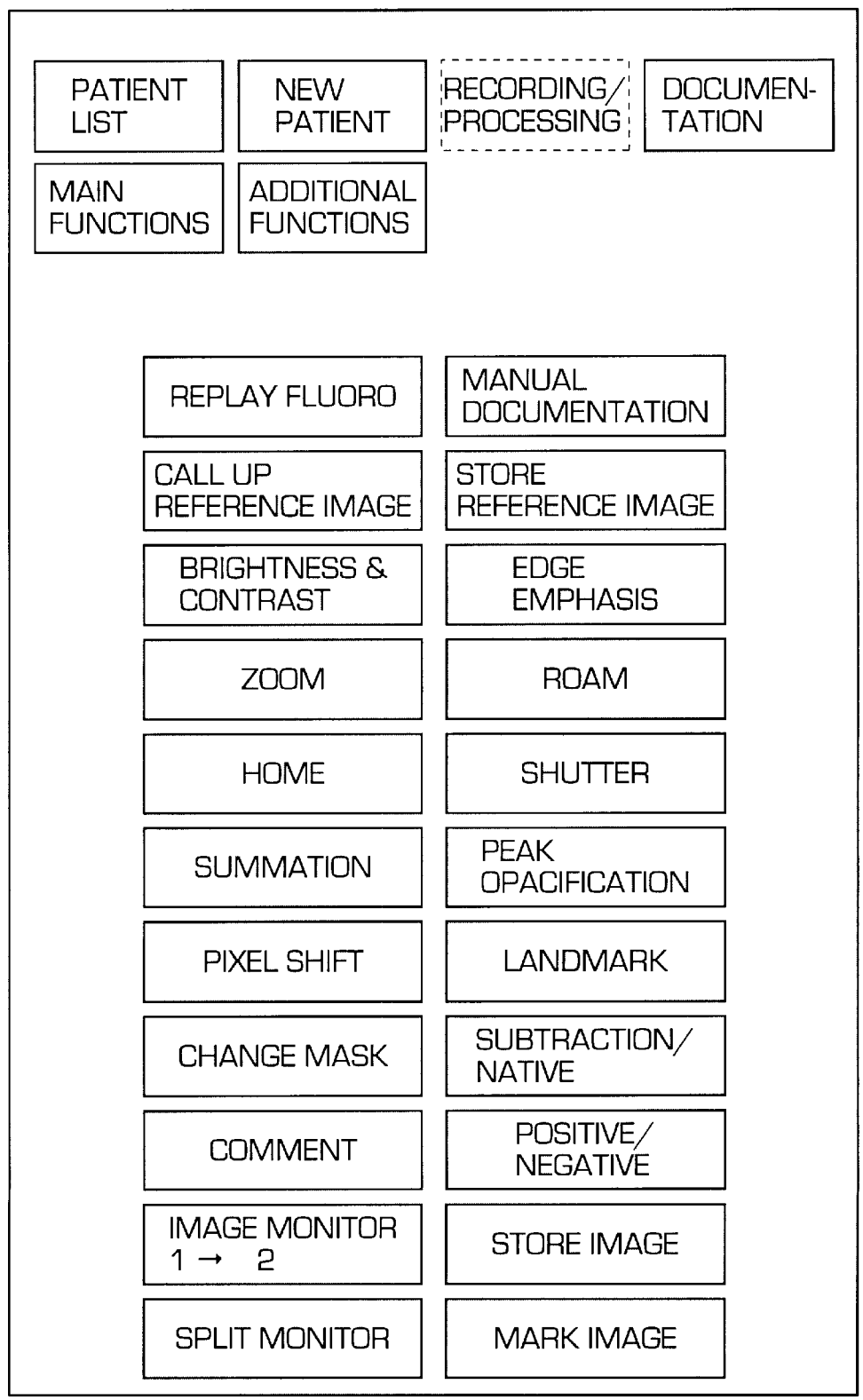

MEDICAL TREATMENT AND OR DIAGNOSTIC SYSTEM

The following disclosure is based on German Patent Application No. 19629093.7, filed on Jul. 18, 1996.

FIELD OF AND BACKGROUND OF THE INVENTION

The invention relates to new and useful improvements in a medical system such as a medical treatment and/or diagnostic system. More particularly, the invention relates to a medical system having a system controller for controlling the system-specific components. The controller works together with an operating unit and is assigned a data storage unit in which it is possible to store at least one operating menu. The operating menu can be called up by means of the operating unit and displayed on a display device. The operating menu comprises a plurality of operating functions which can be selected, if appropriate, by means of a movable marker. When a particular operating function is selected its associated executable system function can be executed under control of the system controller.

Systems of this type, for example an X-ray system, are generally software-controlled multi-component systems comprising, e.g., an X-ray generator, an X-ray tube, a digital, image-amplifier-based image acquisition system, etc. In order to operate the system, menu pages are displayed to the operator on one or more suitable display devices. These menu pages reproduce the total number of stored functions and options that may be selected from this menu and whose associated system function can be executed, given appropriate selection.

The respective menu pages are predefined in terms of their functional composition and layout. That is to say, in the case of a specific menu, all the operating functions associated with that menu are always displayed. In order to be able to control the system appropriately during operation, it is therefore necessary to "leaf through" these various menus. In other words, the system forces the operator to display and select from a plurality of menu pages, e.g., in order to retrieve a desired operating function, or because the operation of a specific operating function requires display of a further submenu, reproducing a subordinate set of functions.

It is also disadvantageous that various components are often controlled via independent menus on various indicating devices, which means that, for example, the X-ray generator is controlled with its specific menus on a different display device than, for example, the digital image processor used thereafter. Thus, in addition to the added time and complexity associated with having to "leaf through" menus, the arrangement described above has an additional disadvantage in that it often is not possible for the user to operate the system from one single indicating device.

OBJECTS OF THE INVENTION

A primary object of the invention is therefore to provide a medical treatment and/or diagnostic system which is configured to be user-friendly and which permits simple, centralized and time-efficient operation.

SUMMARY OF THE INVENTION

These and other objects are achieved by the teaching of the independent claims. Particularly advantageous refinements of the invention are the subject matter of the dependent claims.

In a medical treatment and/or diagnostic system of the type mentioned above, according to the invention, provision is made for the type and/or the number of operating functions, which are assigned to an operating menu displayed on a display device, to be selected on the part of the user and stored in the data storage device as a customized operating menu.

In a system configured according to the invention, the operator is allowed complete freedom in the composition of the system's specific operating menus. If the system is used in a manner whereby only a few preferred operating functions are needed, the operator can compose simply a single operating menu. In short, the user can configure the operating menu in accordance with the user's corresponding requirements. This means that it is possible, for example, for the doctor working on the system to be able to compose a specific menu, comprising a multiplicity of operating functions, that is uniquely suited to the doctor's needs and preferences. In addition, it is possible for another user, such as a medical assistant who works on the same system, to compose a further, customized operating menu for the same system.

Such a system has particular advantage in a work place which is specific with respect to the type of therapy or treatment administered. For example, for a thorax workplace or the like, the operators can compose a specific menu (or various menus) uniquely suited to this workplace. More specifically, the system permits only those operating functions that are actually required and used at this workplace to be indicated in the menu. Extraneous operating functions, which may not even be assigned and which are not necessary for the treatment taking place at this workplace, can be omitted.

Therefore, the system according to the invention permits the operator to structure the menu in a completely free and individual manner, which increases the operating convenience of the system manyfold. The individual operating functions may be present in the respective menu in the form of word characters or string characters or in the form of symbols, or any combination of these.

In order that the operator can compose the menu as simply as possible, in a further refinement of the invention, the system can be arranged to store the individual operating functions that can be assigned to an operating menu in a data storage device. Preferably these operating functions are stored in the form of a list or the like which may, if appropriate, be structured in a function-specific way. It thereby becomes possible for the operator to avoid having to review the entire multiplicity of available operating functions, and, instead, have to look through only those operating functions that are relevant to the operator and then select the desired function from the operating menu in a straight-forward fashion.

In a further refinement of the invention, the multiplicity of operating functions can be displayed on the display device as well, either for the purpose of being selected or for the purpose of structuring the customized operating menu.

The selection of operating functions is still further simplified if the operating functions are stored, as noted above, in the form of a function-specific structured list which is displayed to the operator. It is also possible for this function-specific list to be constructed in the form of submenus, in which case, for each functional area, relating to, e.g., the X-ray generator, the printing of the image, information about the patient, or the like, there is a dedicated menu with operating functions arranged therein. In such a case, the appropriate submenu is displayed whenever the dedicated menu is selected.

In order to further simplify the procedure for composing the individualized menu, the selectable operating functions may be displayed on the display device, simultaneously with and alongside the operating menu to be composed. Additionally, the respectively selected operating function may be displayed essentially directly within the operating menu. Thus, on one half of the screen, a plurality of selectable operating functions are displayed to the operator. On the other half of the screen is an initially unpopulated window, which serves as the space for composing the individual menu. During the composition procedure, immediately after a specific operating function is selected, it is displayed immediately on the second half of the screen, so that the operator can always orient himself or herself as to which operating functions have already been selected. This allows the operator to decide whether still additional functions are to be accommodated, or whether the menu is structured in a manner sufficiently specific to the user and workplace.

On the basis of the invention, a marker can be displayed on the display device, for selecting the respective operating function or functions. The marker can be moved, e.g., by a selection means assigned to the operating unit, such as a joystick, a mouse, a track ball, a sensor field, a scanning field, or a light pen, allowing trouble-free and simple selection by the user.

As an alternative to the use of a selection means as described above, the display device to be provided with a touch-sensitive surface (touchscreen). This approach has the advantage of enabling direct selection of an operating function. The operator, by touching the surface of the display device in the region indicating the operating function to be selected, can choose the operating function in a particularly simple way. In this case, the indicating device can be designed as a monitor or as a display panel.

In order to be able to increase the operating convenience of the entire treatment and/or diagnostic system still further, the display device can be arranged adjacent to a further display device, in the form of e.g. a monitor, used to display a subject area being treated and/or examined. This configuration allows the control display and the display of the subject area to be arranged in relation to and proximate to one another, such that they are both in the field of view of the person operating the system, e.g., a treating physician or a medical staff member. This arrangement avoids inconveniencing the operator in having to look at different display devices located at different positions in order on the one hand to operate the system and on the other hand to study the specific area being examined. The arrangement according to the invention thus not only renders the medical system more efficient and user-friendly but has the additional benefit of improving the overall safety associated with the operation of the treatment and/or diagnostic system.

According to yet another particularly expedient aspect of the invention, the display device can be designed as a combined display device for simultaneously displaying the operating menu and one or more areas being examined and/or treated. Accordingly, all the data which are of interest to the operator, i.e., the operating functions and the subject area being treated, are displayed to the operator on a single display device. As a result, all relevant information is located in the field of view of the operator, which renders operation of the system even more convenient.

BRIEF DESCRIPTION OF THE DRAWINGS

The invention, including further advantages, features and refinements of the invention, is explained in more detail below with the aid of diagrammatic, exemplary embodiments in the drawing, in which:

FIG. 4 shows an example of an operating menu, displayed on a display device, according to the conventional art.

DETAILED DESCRIPTION OF THE PREFERRED EMBODIMENTS

The conventional art is first explained, with reference to FIG. 4, in order to describe the disadvantages and limitations associated with the conventional art. FIG. 4 shows, by way of example, an operating menu which is reproduced on an indicating device, for example a monitor. The operating menu is predefined in terms of its composition of the selectable operating functions. The particular operating menu illustrated is used for the operation of components and functions relating to the digital image processing operation of the medical system. Functional control for operating, e.g., the high-voltage generator of an X-ray source is not possible from within this menu. Instead, the menu which is necessary for this latter aspect of the system is reproduced on another indicating device.

FIG. 4 further shows, by way of example, the submenu located under the main menu "Recording/ Processing". This main operating menu is bordered by a dashed line in the Figure for clarity. In the status illustrated, the operator has selected this main menu "Recording/Processing", which has caused the appropriate subfunctions to be displayed. The subfunctions forming the submenu are displayed below the main menu and are available to the operator for selection. The structuring of these subfunctions is predefined in a fixed manner, that is to say these subfunctions and no others are currently available for selection. If the operator, continuing to operate the system, wishes to call up a further subfunction that is currently not indicated, the operator must first select the appropriate entry on the main menu corresponding to the other operating function and then proceed from there to the appropriate subfunction. For example, if the operator wishes to proceed from a "Recording/Processing" task to a "Documentation" task, then the operator must exit the "Recording/ Processing" screen and locate the subsequent, desired operating subfunction, which is currently hidden from view. In other words, the operator must first select the main menu "Documentation", in order that the operating functions arranged under it will be displayed, and only then can the operator proceed with selecting the actual subfunction of interest. This means that the operator must move laboriously from menu to menu in order to get within the access range of the desired functions, in order that the latter can be chosen and executed.

Figure 1:
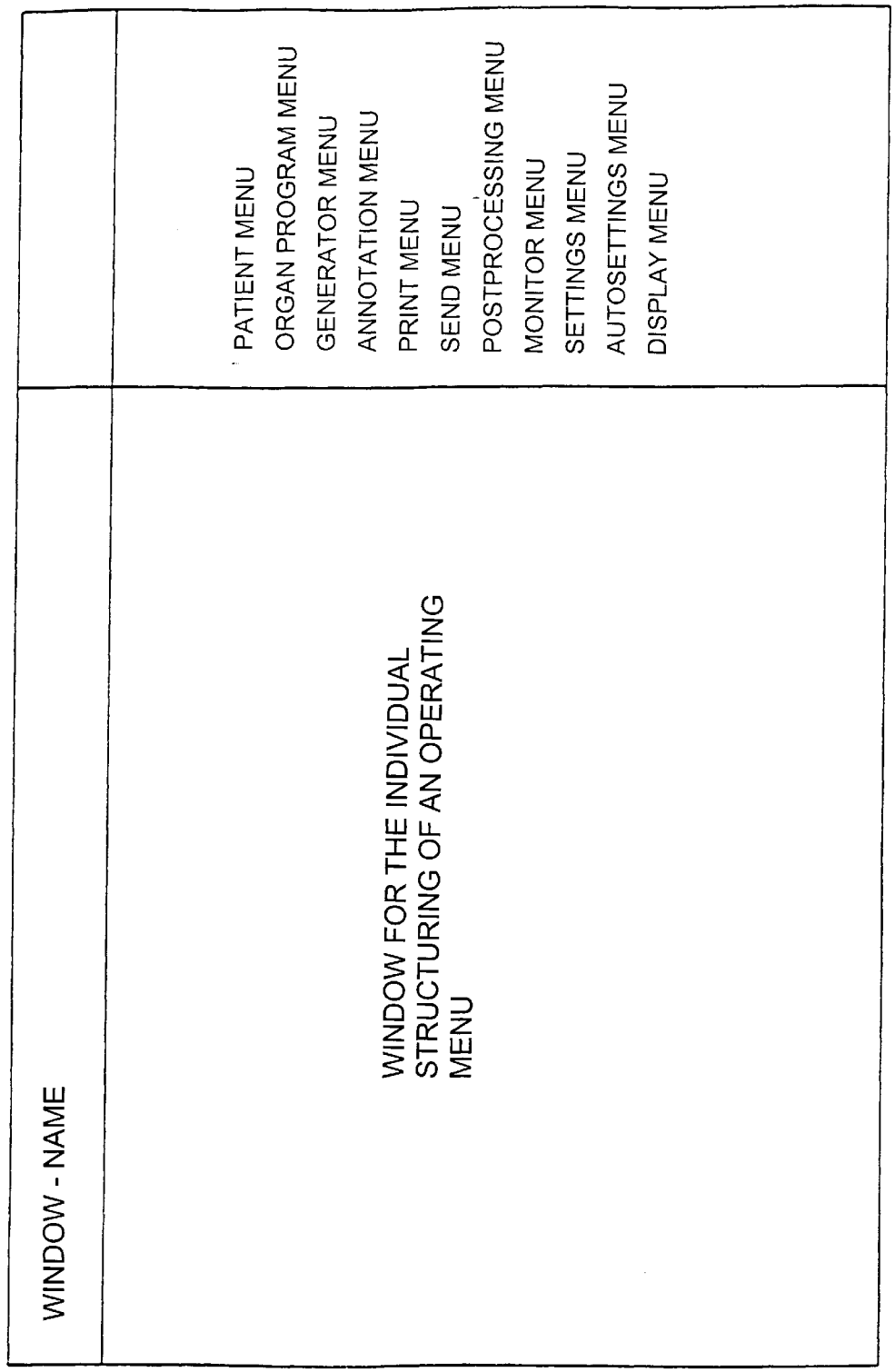
FIG. 1 shows the screen of a display device having an area displaying the selectable operating functions in menu form and a separate area used for individual menu configuration.

FIG. 1 shows an indicating device which is structured according to the invention. On this indicating device, in the right-hand area, a multiplicity of different menus are displayed, which in the present embodiment are structured as main menus. A series of subfunctions are assigned and "lie behind" respective ones of the main menus. The menus, as well as the respective subfunctions or operating functions lying behind them, are displayed as word characters in the example shown. Alternatively, they can be reproduced in the form of symbols or the like, or as a combination of characters and symbols.

The far larger area of the indicating device shown in FIG. 1 is free of information prior to the composition of a customized menu. This larger area serves to display the selected functions once the screen has been customized. Thus, this area permits an operator to create a specific, individualized menu, matched in a function-specific manner, e.g., to the type of workplace or to the type of professional activity. According to the invention, an operator wishing to create such a customized menu uses, e.g., a marker (not shown), such as a cursor, pointer, or other indicator to select, e.g., the menu "Print", in order to access the associated submenu. As a result, the individual operating functions stored underneath the "Print" menu are displayed in the right-hand area. From the multiplicity of operating functions, specific individual functions can then be selected and taken over into the adjacent display area and incorporated into the new operating menu. As a further example, by choosing the menu "Send", the operating functions arranged under this menu can consequently be displayed and selected for inclusion in the individualized portion of the screen, which is ultimately true for each of the menus shown in FIG. 1. Once completed, the selected functions are available to be selected directly whenever the customized operating menu is called up.

As can be seen from FIG. 1, in addition to the menus relating essentially to digital image processing, a "generator" menu is also stored. Located under this menu are all the operating functions which are required for the operation of the generator. In contrast to the conventional art, these operating functions can be incorporated into this operating menu along with the image processing functions, so that they can be selected directly without having to view or interact with a separate indicating device.

Figure 2:
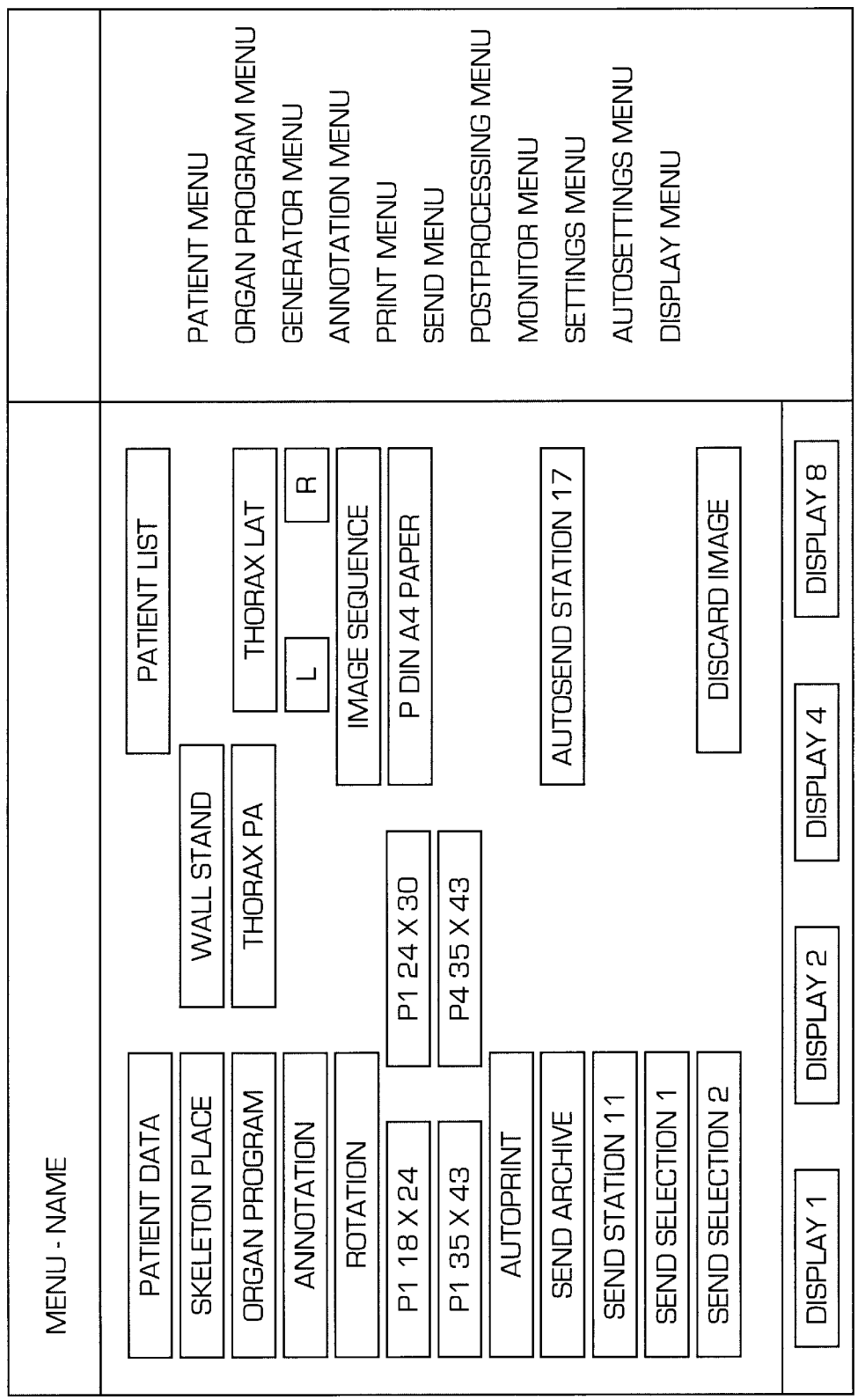
FIG. 2 shows an example of an individually composed operating menu used for a skeleton workstation/thorax wallstand.

A specific example of an individually composed operating menu for a skeleton workplace/thorax wall stand is shown in FIG. 2. As can be seen from the table reproduced below, the operating functions indicated in the operating menu are selected based on individual preference and requirements from the various main menus. Such an arrangement enables the incorporation of the widest possible range of functions into a single operating menu, without it being necessary to "leaf through" various menu pages. Of course, it may be necessary to resort to a different specific operating menu if a particular operator needs a less routine function or if the operator must resort to so many operating functions that there is not sufficient space within one menu window. However, under normal circumstances, the invention provides an operating menu containing not only a wide range of different functions but also those functions in particular that are most commonly used in practice.

According to another preferred embodiment, composing the customized menu can be carried out in a particularly simple way, by means of a marker. The marker is used to select the respective menu or the appropriate operating function via a mouse or the like. Aided by the software, the selected menu or function is simply dragged across into the customized menu area, whereby the system writes appropriate data to an appropriate storage area, so that the selection is displayed thereafter in the customized area.

TABLE

| Operating functions | Origin |
|---|---|
| Patient data | Patient menu |
| Patient list | Patient menu |
| Skeleton place | Generator menu |
| Wall stand | Generator menu |
| Organ program | Generator menu |
| Thorax pa | Generator menu |
| Thorax lat | Generator menu |
| Annotation | Annotation menu |
| L | Annotation menu |
| R | Annotation menu |
| Rotation | Postprocessing menu |
| Image sequence | Postprocessing menu |
| P1__18x24 | Print menu |
| P1__24x30 | Print menu |
| P1__35x43 | Print menu |
| P4__35x43 | Print menu |
| P DIN A4 Paper | Print menu |
| Autoprint | Print menu |
| Send archive | Send menu |
| Send station 11 | Send menu |
| Send selection 1 | Send menu |
| Send selection 2 | Send menu |
| Autosend station 17 | Send menu |
| Discard image | Postprocessing menu |
| Display 1 | Display menu |
| Display 2 | Display menu |
| Display 4 | Display menu |
| Display 8 | Display menu |

Figure 3:
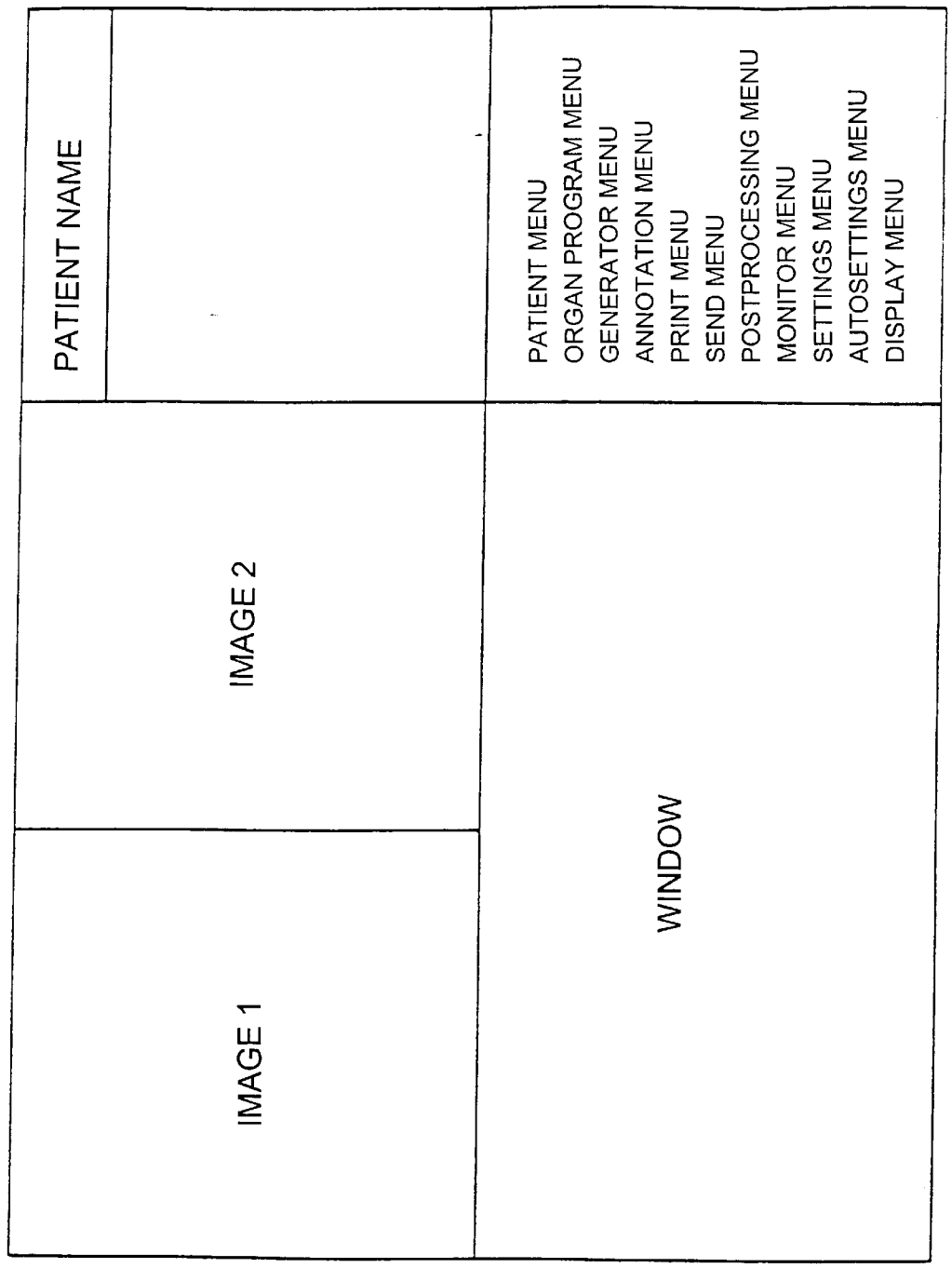
FIG. 3 shows a further embodiment, where the screen of the display device is further subdivided.

FIG. 3 illustrates a further embodiment involving the display format, according to which the screen displayed on the display device is further subdivided. In this embodiment, as is the case in the embodiment of FIG. 1, an area having selectable menus and a window area for creating the individual operating menu are again provided. In addition, two further areas "Image 1" and "Image 2" are provided for displaying two different images of an area, currently being examined, of the patient to be treated. As a result, all the information which is necessary for both operating the system and for diagnosing and/or treating the area under examination is available to the treating doctor on a single display device. The system according to the embodiment of FIG. 3 additionally provides yet another area relating to specific patient information, such as, e.g., the patient's name and/or other identifying information.

Figure 5:
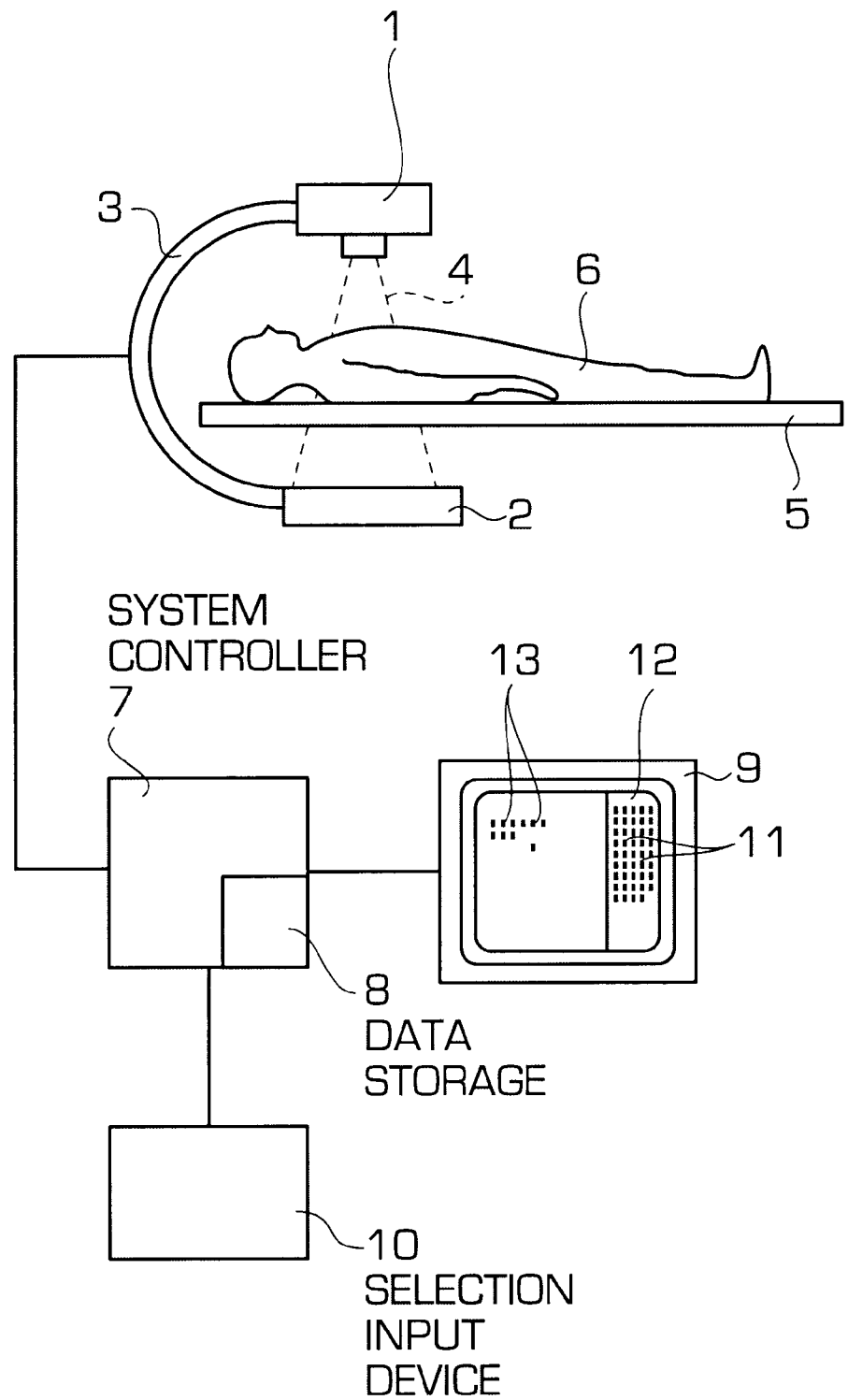
FIG. 5 is a schematic diagram of a medical system according to a preferred embodiment of the invention.

FIG. 5 shows a schematic diagram of a medical system according to the invention embodied by way of example as an X-ray system. The X-ray system includes an X-ray source 1 and an associated X-ray detector 2. According to the embodiment illustrated, the X-ray source 1 and detector 2 are both fastened to a C-frame support 3. In operation, the X-ray source 1 emits X-ray radiation 4, which radiates through a patient 6 positioned on a patient table 5. Radiation received by the detector 2 is output as electrical signals to a system controller 7 for further processing and eventual display as a radiation image. The system controller 7 additionally controls the various components of the X-ray system. The system controller 7 includes a data storage unit 8 (e.g., memory), which stores not only general operational data but also operating menus for selecting specific operating functions of the x-ray system. The operating functions are capable of being displayed on a display device 9 that is connected to the system controller 7 and that takes the form, e.g., of a monitor or display. The operating functions are executable by means of the system controller 7. The system controller 7 is connected also to a selection input device 10, which, for example, can include a joystick, a mouse, a track ball, a sensor field, a scanning field, or a light pen or the like. The selection input device 10 can be used, e.g., for retrieving the operating menus stored in the data storage unit 8. Alternatively or additionally, the display device 9 may be fashioned with a touchscreen, whereby menus and functions can be selected by direct manual contact with the screen itself.

FIG. 5 illustrates an arrangement on the screen of the display device 9 analogous to that shown in FIG. 1. In other words, a plurality of operating menus or main menus 11 are displayed on the right side of the display. These menus can be selected by means of a marker 12 (e.g., cursor) that is controlled and is moveable by the selection input device 10. Following selection of a desired operating menu, those operating functions classified under that operating menu are displayed on the display device 9 accordingly. The operating functions are, e.g., stored in the data storage unit 8 in the form of a structured list. From these displayed operating functions it is then possible to select the desired operating functions, e.g., by using the marker 12, and thereby allocate them to the individualized operating menu. This customized menu occupies the left portion of the display in the embodiment illustrated. In the illustrated example, the user has already selected two operating functions 13 for the customized menu. Once the user has finished composing the customized menu, the menu is stored in the data storage unit 8. Then, when the X-ray system is next set in operation, the user can call up the individualized menu, whereby all the operating functions of importance to that user are directly accessible and available for selection. As an alternative to the arrangement shown in FIG. 5, it is of course also possible to arrange the display differently, e.g., as shown in FIG. 3.

Figure 6:
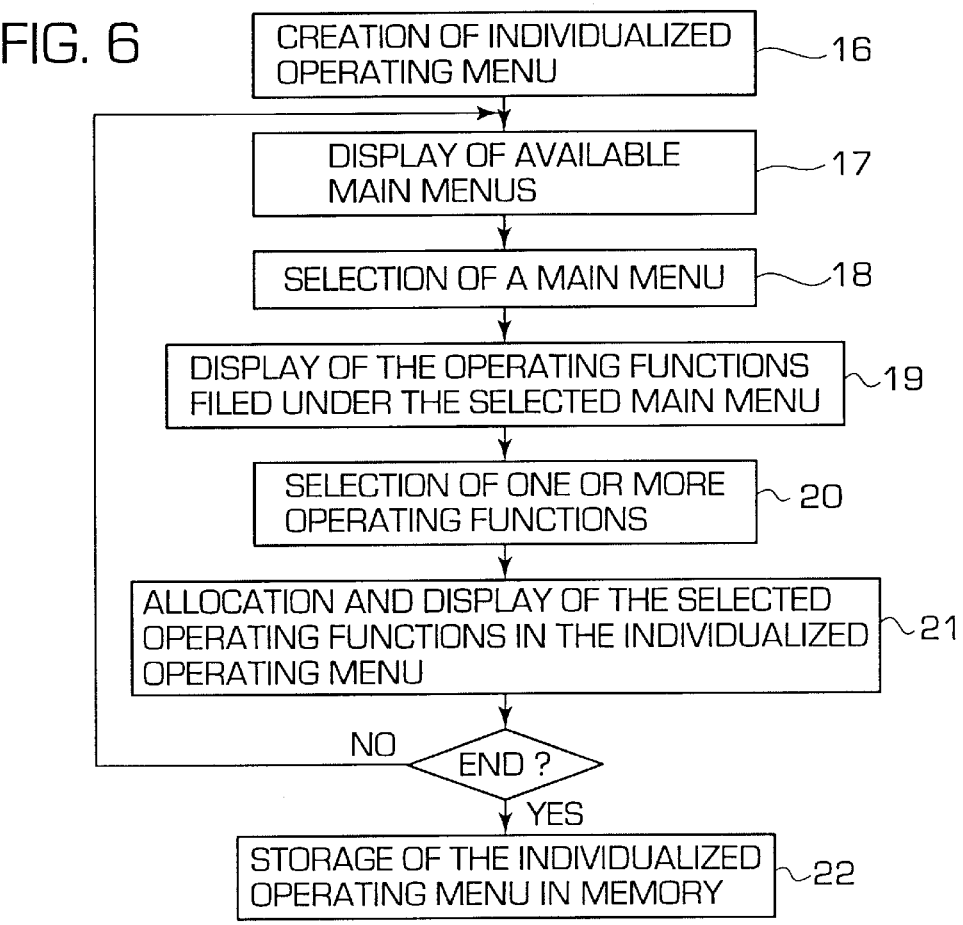
FIG. 6 is a flowchart illustrating the process steps for creating an individualized operating menu according to a preferred embodiment of the invention.

FIG. 6 illustrates, in the form of a flowchart, a process for creating an individualized operating menu. As shown in Step 16, the user initially selects the function for creating an individualized operating menu. Thereafter, all of the main menus available for composing an individualized operating menu are displayed on the display device 9 (Step 17). In Step 18, the user selects the desired main menu from which the user intends to select one or more operating functions. Once the desired main menu is selected, all of the actual operating functions classified thereunder are displayed in Step 19. It is now possible, as shown in Step 20, for the user to select one or more operating function from the main menu for inclusion in the customized menu. When the selection process is complete, the selected operating functions are allocated automatically to the individualized operating menu and displayed in the appropriate window for the individualized menu, in accordance with Step 21. If the user has finished compiling the individualized menu, then the user can exit the process for creating the individualized operating menu, whereby the system controller 7 causes the individualized operating menu to be stored, in Step 22, in an appropriate location of the data storage unit 8. However, in case the user wishes to include additional operating functions from other main menus in the individualized menu, then the processing returns the user to Step 17, as shown in FIG. 6. In this case, the processing Steps 17–21 are repeated as needed until the customized menu is complete and the user exits the menu creation algorithm.

Figure 7:
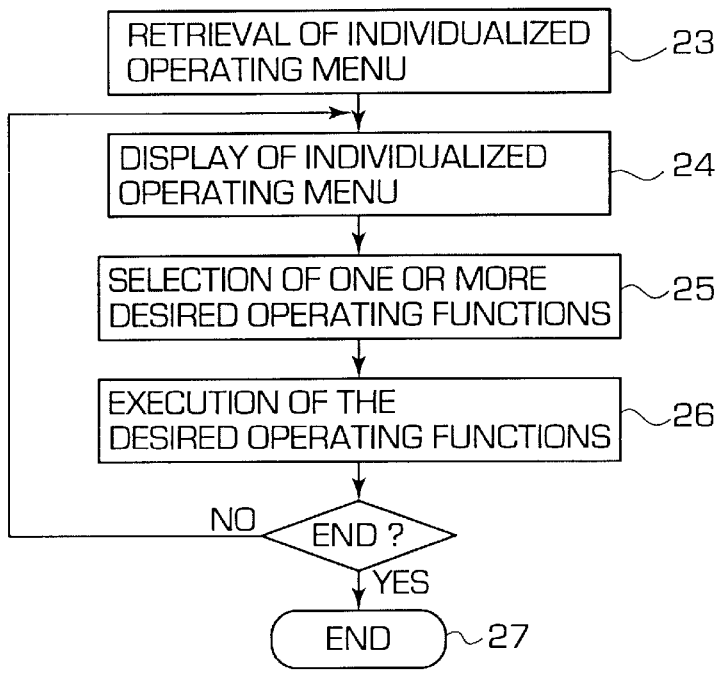
FIG. 7 is a flowchart illustrating, by way of example, operational control of the medical system utilizing an individualized operating menu.

FIG. 7 illustrates the operation of the described system in accordance with a customized menu. The user first selects his or her customized menu, which is then retrieved from storage in the data storage unit 8 (Step 23) and subsequently displayed on the display device 9 (Step 24). Now, the user can select one or more of the operating functions, as desired, all from within the same operating menu (Step 25). These are then executed under the control of the system controller 7 in Step 26. Once the selected operating functions have been carried out, if no additional executable functions are required to be performed, operation of the system can be ended. However, in the event that, e.g., a diagnostic procedure is not yet completed and additional operating functions remain to be carried out, the processing returns to Step 24, thereby permitting the user to continue selecting desired operating functions.

The above description of the preferred embodiments has been given by way of example. From the disclosure given, those skilled in the art will not only understand the present invention and its attendant advantages, but will also find apparent various changes and modifications to the structures disclosed. It is sought, therefore, to cover all such changes and modifications as fall within the spirit and scope of the invention, as defined by the appended claims, and equivalents thereof.

What is claimed is:

1. A medical system comprising:
   a system controller for controlling components of the system;
   a data storage unit assigned to said system controller for storing at least one operating menu;
   a selection input device associated with said system controller for allowing a user to retrieve and select from the at least one operating menu; and
   an indicating device for displaying the at least one operating menu, wherein:
   the at least one operating menu comprises a plurality of operating functions which are selectable by means of said selection input device to cause said system controller to execute an executable system function associated with the operating function selected, and
   the operating functions are further selectable by means of said input device to cause said system controller to store the selected operating functions in said data storage device as an independent operating menu separate from the at least one operating menu.

2. The medical system as claimed in claim 1, wherein the plurality of operating functions are assigned respectively to one of a plurality of operating menus stored in said data storage device in accordance with a functional grouping to thereby define submenus of the operating functions.

3. The medical system as claimed in claim 1, wherein:
   said selection input device is incorporated into said indicating device, and
   the plurality of operating functions are displayable by means of said indicating device and, while being displayed, are selectable by means of said indicating device for allowing the user to compose the independent operating menu.

4. The medical system as claimed in claim 3, wherein said indicating device comprises a touchscreen as said selection input device.

5. The medical system as claimed in claim 1, wherein:
   the plurality of operating functions of the at least one operating menu are displayed alongside the independent operating menu by means of said indicating device, and
   the selected operating functions are displayed directly in the independent operating menu.

6. The medical system as claimed in claim 1, wherein said system controller generates a marker for display on said indicating device, which marker is movable by means of said selection input device and which marker allows the user to select from among the selectable operating functions to compose the independent operating menu.

7. The medical system as claimed in claim 6, wherein said selection input device comprises at least one of a joystick, a mouse, a track ball, a sensor field, a scanning field, and a light pen for allowing the user to move the marker.

8. The medical system as claimed in claim 1, wherein said indicating device comprises a monitor.

9. The medical system as claimed in claim 1, wherein said indicating device is positioned adjacent to a monitor of the medical system that displays an area under examination.

10. The medical system as claimed in claim 1, wherein said indicating device comprises a screen arranged to simultaneously display at least the independent operating menu and an image of an area under examination.

11. The medical system as claimed in claim 1, wherein:
the independent operating menu is retrievable by means of said selection input device to be displayed by means of said indicating device, and
the selected operating functions are designatable from the independent operating menu by means of said selection input device to cause said system controller to execute an executable system function associated with the designated operating function.

12. The medical system as claimed in claim 1, wherein:
said components of the system comprise components for performing a medical treatment of a patient, and
the executable system function is at least one step in the medical treatment.

13. The medical system as claimed in claim 1, wherein:
said components of the system comprise components for performing a diagnostic procedure of a patient, and
the executable system function is at least one step in the diagnostic procedure.

14. A medical system comprising:
a system controller for controlling components of the system;
a data storage unit assigned to said system controller for storing a plurality of operating menus retrievable by means of said system controller and for storing a plurality of operating functions, each said operating function being associated with an executable function of the system;
a selection unit associated with said system controller for allowing a user to retrieve and select from the operating menus; and
a display device associated with said system controller for displaying a first display field, in which the plurality of operating menus are displayed, simultaneously with and alongside a second display field for displaying selected ones of the operating functions,
wherein the selected operating functions displayed in the second display field are included and arranged in the second display field in accordance with a customization operation whereby a user selects desired operating functions from the operating menus, and
wherein the selected operating functions are stored in said data storage unit as a customized operating menu.

15. The medical system as claimed in claim 14, wherein:
said components of the system comprise components for performing a medical treatment of a patient, and
the executable function of the system is at least one step in the medical treatment.

16. The medical system as claimed in claim 14, wherein:
said components of the system comprise components for performing a diagnostic procedure of a patient, and
the executable function of the system is at least one step in the diagnostic procedure.

* * * * *